United States Patent
Mellema et al.

(10) Patent No.: US 12,023,199 B2
(45) Date of Patent: *Jul. 2, 2024

(54) SYSTEMS AND METHODS FOR ULTRASOUND ELASTOGRAPHY WITH CONTINUOUS TRANSDUCER VIBRATION

(71) Applicant: Mayo Foundation for Medical Education and Research, Rochester, MN (US)

(72) Inventors: Daniel C. Mellema, Rochester, MN (US); Pengfei Song, Rochester, MN (US); Matthew W. Urban, Rochester, MN (US); Armando Manduca, Rochester, MN (US); James F. Greenleaf, Rochester, MN (US); Shigao Chen, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 835 days.

This patent is subject to a terminal disclaimer.

(21) Appl. No.: 15/766,327

(22) PCT Filed: Oct. 6, 2016

(86) PCT No.: PCT/US2016/055649
§ 371 (c)(1),
(2) Date: Apr. 5, 2018

(87) PCT Pub. No.: WO2017/062553
PCT Pub. Date: Apr. 13, 2017

(65) Prior Publication Data
US 2018/0296191 A1    Oct. 18, 2018

Related U.S. Application Data

(60) Provisional application No. 62/238,891, filed on Oct. 8, 2015.

(51) Int. Cl.
*A61B 8/08*    (2006.01)
*A61B 5/00*    (2006.01)
(Continued)

(52) U.S. Cl.
CPC ............ *A61B 8/485* (2013.01); *A61B 5/0051* (2013.01); *A61B 8/4254* (2013.01);
(Continued)

(58) Field of Classification Search
CPC ... A61B 5/0051; A61B 5/0053; A61B 8/4254; A61B 8/485; A61B 8/5207;
(Continued)

(56) References Cited

U.S. PATENT DOCUMENTS 5,524,636 A    6/1996    Sarvazyan
5,810,731 A *  9/1998    Sarvazyan ............... A61B 8/08
                                                  600/438

(Continued)

FOREIGN PATENT DOCUMENTS

CN    102149429    *    8/2011
CN    102151152 A       8/2011
(Continued)

OTHER PUBLICATIONS

T. Sugimoto et al. "Tissue hardness measurement using the radiation force of focused ultrasound." IEEE Symposium on Ultrasonics 1990.*

(Continued)

*Primary Examiner* — Patrick Fernandes
*Assistant Examiner* — Nicholas A Robinson
(74) *Attorney, Agent, or Firm* — Quarles & Brady LLP

(57) ABSTRACT

Systems and methods for processing data acquired using ultrasound elastography, in which shear waves are generated in a subject using continuous vibration of an ultrasound transducer, are provided. The systems and methods (Continued)

described here can effectively remove motion artifacts associated with vibration of the ultrasound transducer, and can also remove the data sampling misalignment caused when a line-by-line imaging mode is used to acquire data, as is done by many conventional ultrasound scanners. Thus, the systems and methods described here provide techniques for transducer motion correction and for aligning motion signals detected by line-by-line scanning ultrasound systems.

5 Claims, 6 Drawing Sheets

(51) Int. Cl.
*A61B 8/00* (2006.01)
*G01S 7/52* (2006.01)
*G01S 15/89* (2006.01)

(52) U.S. Cl.
CPC .......... *A61B 8/5207* (2013.01); *A61B 8/5223* (2013.01); *A61B 8/5276* (2013.01); *G01S 7/52042* (2013.01); *G01S 7/52079* (2013.01); *G01S 15/8915* (2013.01); *A61B 5/0053* (2013.01)

(58) Field of Classification Search
CPC . A61B 8/5223; A61B 8/5276; G01S 15/8915; G01S 7/52042; G01S 7/52079
See application file for complete search history.

(56) References Cited

U.S. PATENT DOCUMENTS

| | | | |
|---|---|---|---|
| 5,983,162 A | 11/1999 | Huang | |
| 6,329,821 B1 | 12/2001 | Zhou | |
| 6,511,427 B1 | 1/2003 | Sliwa, Jr. | |
| 6,770,033 B1 | 8/2004 | Fink | |
| 7,444,875 B1 | 11/2008 | Wu | |
| 7,578,789 B2 | 8/2009 | Sandrin | |
| 7,785,259 B2 | 8/2010 | Zheng | |
| 7,975,555 B2 | 7/2011 | Zhuang | |
| 8,602,994 B2 | 12/2013 | Zheng | |
| 8,660,848 B1 | 2/2014 | Humi | |
| 8,734,350 B2 | 5/2014 | Greenleaf | |
| 8,837,798 B2 | 9/2014 | Li | |
| 10,779,799 B2* | 9/2020 | Chen | A61B 8/485 |
| 2004/0068184 A1* | 4/2004 | Trahey | G01S 15/8927 600/437 |
| 2004/0225215 A1* | 11/2004 | Querleux | A61B 8/485 600/437 |
| 2005/0119568 A1 | 6/2005 | Salcudean | |
| 2005/0252295 A1* | 11/2005 | Fink | G01S 7/52022 73/603 |
| 2005/0267695 A1 | 12/2005 | German | |
| 2007/0038095 A1* | 2/2007 | Greenleaf | A61B 8/485 600/438 |
| 2007/0093716 A1 | 4/2007 | Radulescu | |
| 2007/0167805 A1* | 7/2007 | Clement | A61B 8/13 600/459 |
| 2009/0182234 A1 | 7/2009 | Perrey | |
| 2009/0304246 A1 | 12/2009 | Walker | |
| 2010/0168566 A1* | 7/2010 | Bercoff | G01S 7/52036 600/438 |
| 2010/0256530 A1* | 10/2010 | Varghese | A61B 5/0051 600/587 |
| 2010/0286516 A1 | 11/2010 | Fan | |
| 2010/0312116 A1* | 12/2010 | Pernot | A61B 8/0883 600/453 |
| 2011/0201931 A1 | 8/2011 | Palmeri | |
| 2011/0263978 A1* | 10/2011 | Chen | A61B 8/485 600/438 |
| 2012/0123263 A1 | 5/2012 | Osaka | |
| 2012/0123562 A1 | 5/2012 | Oster | |
| 2012/0215101 A1 | 8/2012 | Maleke | |
| 2012/0226158 A1 | 9/2012 | Greenleaf | |
| 2012/0269414 A1 | 10/2012 | Zha | |
| 2013/0237820 A1* | 9/2013 | Vappou | A61B 8/0858 600/438 |
| 2013/0289402 A1* | 10/2013 | Tabaru | G01S 7/52049 600/438 |
| 2013/0296698 A1 | 11/2013 | Fraser | |
| 2014/0046173 A1* | 2/2014 | Greenleaf | G16H 50/30 600/411 |
| 2014/0147012 A1 | 5/2014 | Park | |
| 2014/0147013 A1 | 5/2014 | Shandas | |
| 2014/0296709 A1* | 10/2014 | Fatemi | A61B 8/5223 600/438 |
| 2014/0330122 A1* | 11/2014 | Baghani | A61B 8/463 600/438 |
| 2015/0126867 A1* | 5/2015 | Osumi | A61B 8/06 600/438 |
| 2015/0216507 A1 | 8/2015 | Greenleaf | |
| 2017/0156701 A1 | 6/2017 | Urban | |
| 2017/0333005 A1 | 11/2017 | Chen | |
| 2017/0340310 A1* | 11/2017 | Carlini | A61B 8/485 |
| 2018/0296191 A1 | 10/2018 | Mellema | |
| 2019/0175150 A1* | 6/2019 | Labyed | A61B 8/485 |

FOREIGN PATENT DOCUMENTS

| | | |
|---|---|---|
| CN | 102782518 A | 11/2012 |
| JP | H08191834 | 7/1993 |
| JP | 2008539005 | 11/2008 |
| WO | 2009140607 | 11/2009 |
| WO | 2012080913 A1 | 6/2012 |
| WO | 2013026141 A1 | 2/2013 |
| WO | 2013160468 | 10/2013 |
| WO | 2014055973 | 4/2014 |
| WO | 2014128182 | 8/2014 |
| WO | 2016067072 A1 | 5/2016 |
| WO | 2016069750 A1 | 5/2016 |
| WO | WO-2016108178 A1 * | 7/2016 ......... A61B 8/08485 |
| WO | 2017062553 A1 | 4/2017 |

OTHER PUBLICATIONS

K. Nightingale et al. "Shear-wave generation using acoustic radiation force: in vivo and ex vivo results." Ultrasound Med Biol. Dec. 2003; 29(12):1715-23.*

Cortes et al. "Continuous Shear Wave Elastography: A New Method to Measure in-vivo Viscoelastic Properties of Tendons." Ultrasound Med Biol. Jun. 2015; 41(6): 1518-1529. Published online Mar. 19, 2015.*

L. Sandrin, M. Tanter, J. .-L. Gennisson, S. Catheline and M. Fink, "Shear elasticity probe for soft tissues with 1-D transient elastography," in IEEE Transactions on Ultrasonics, Ferroelectrics, and Frequency Control, vol. 49, No. 4, pp. 436-446, Apr. 2002, doi: 10.1109/58. 996561. (Year: 2002).*

European Patent Office Supplementary Search Report for application 16854283.5, dated Jun. 4, 2019, 14 pages.

Azar, R Z, et al. "2-D high-frame-rate dynamic elastography using delay compensated and angularly compounded motion vectors: preliminary results." IEEE transactions on ultrasonics, ferroelectrics, and frequency control 57.11 (2010).

Baghani, A. et al., in "A high-frame-rate ultrasound system for the study of tissue motions," IEEE Trans. Ultrason. Ferroelectr. Freq. Control, 2010; 57:1535-1547.

Bamber, J. et al., "EFSUMB guidelines and recommendations on the clinical use of ultrasound elastography. Part 1: Basic principles and technology," Ultraschall in Der Medizin, vol. 34, pp. 169-184, Apr. 2013.

Bamberger R.H. et al., "A filter bank for the directional decomposition of images: Theory and design," IEEE Trans. Signal Process., vol. 40, p. 11, Apr. 1992.

Barr, R.G. et al., "Elastography Assessment of Liver Fibrosis: Society of Radiologists in Ultrasound Consensus Conference Statement," Radiology, vol. 276, pp. 845-861, Sep. 2015.

(56) References Cited

OTHER PUBLICATIONS

Bercoff, J. et al., "Supersonic shear imaging: A new technique for soft tissue elasticity mapping," IEEE Trans. Ultrason., Ferroelectr., Freq. Control, vol. 51, pp. 396-409, Apr. 2004.
Chen, S.G. et al., "Shearwave Dispersion Ultrasound Vibrometry (SDUV) for Measuring Tissue Elasticity and Viscosity," IEEE Trans. Ultrason., Ferroelectr., Freq. Control, vol. 56, pp. 55-62, Jan. 2009.
China National Intellectual Property Administration, First Office Action for application 201580059146.6, dated Jul. 3, 2019, with associate translation.
Daubechies, I. et al. "Synchrosqueezed Wavelet Transforms: an Empirical Mode Decomposition-like Tool.", Year: 2010.
Deffieux, T., et al. "On the effects of reflected waves in transient shear wave elastography." IEEE transactions on ultrasonics, ferroelectrics, and frequency control 58.10 (2011): 2032-2035.
Eskandari, H., et al. "Identifying malignant and benign breast lesions using vibroelastography." 2013 IEEE International Ultrasonics Symposium (IUS). IEEE pp. 25-28, 2013.
European Patent Office Supplementary Search Report for PCT/US2015/057825 dated Aug. 9, 2018.
Huang, N. E. et al, "Applications of Hilbert-Huang transform to non-stationary financial time series analysis," Appl. Stochastic Models in Bus. and Industry, vol. 19, pp. 245-268, Jul.-Sep. 2003.
Huang, N. E. et al, "The empirical mode decomposition and the Hilbert spectrum for nonlinear and non-stationary time series analysis," Proc. of the Royal Soc. of London: Math. Physical and Eng. Sci., vol. 454, pp. 903-995, Mar. 8, 1998.
International Search Report and Written Opinion dated Jan. 19, 2016 in connection with PCT/US2015/057825.
International Searching Authority, International Search Report and Written Opinion for application PCT/US2018/045965, dated Oct. 24, 2018.
Japan Patent Office, Japanese Office Action for application 2017-523369, dated Jul. 2, 2019, with associate translation.
Kasai C., et al., in "Real-time two-dimensional blood flow imaging using an autocorrelation technique," IEEE Trans. on Sonics Ultrason., 1985; 32(3):458-464.
Knutsson, H. et al, in "Local multiscale frequency and bandwidth estimation," Proc. IEEE Int. Conf. Image Process., 1994.
Linderhed A., "Image compression based on empirical mode decomposition," in Proc. of SSAB Symp. Image Anal., 2004, pp. 110-113.
Lu Y. M. et al, "Multidimensional directional filter banks and surfacelets," IEEE Trans. Image Process., vol. 16, pp. 918-931, Apr. 2007.
Manduca, A. et al, "Magnetic resonance elastography: non-invasive mapping of tissue elasticity," Medical Image Anal., vol. 5, pp. 237-254, Dec. 2001.
Manduca, A. et all, "Image processing for magnetic resonance elastography", Proc. SPIE, vol. 2710, pp. 616-623 1996.
McAleavey, S.A. et al, "Shear-modulus estimation by application of spatially-modulated impulsive acoustic radiation force," Ultrason. Imaging, vol. 29, pp. 87-104, Apr. 2007.
Mellema, D.C. et al, "Probe Oscillation Shear Elastography (PROSE): A High Frame-Rate Method for Two-Dimensional Ultrasound Shear Wave Elastography," IEEE Trans. Med. Imag., vol. 35, pp. 2098-2106, Sep. 2016.
Nightingale, K. et al, "Shear-wave generation using acoustic radiation force: In vivo and ex vivo results," Ultrasound in Medicine and Biology, vol. 29, pp. 1715-1723, Dec. 2003.
Parajuli, RK, et al. "Shear wave imaging using phase modulation component of harmonic distortion in continuous shear wave excitation." Japanese Journal of Applied Physics 52.7S (2013): 07HF22.
Peng, Z.K. et al, "A comparison study of improved Hilbert-Huang transform and wavelet transform: Application to fault diagnosis for rolling bearing," Mech. Syst. and Signal Process., vol. 19, pp. 974-988, Sep. 2005.
Rilling, G. et al, "Bivariate empirical mode decomposition," IEEE Signal Process. Lett., vol. 14, pp. 936-939, Dec. 2007.
Rilling, G. et al, "On empirical mode decomposition and its algorithms," in IEEE-EURASIP workshop on nonlinear signal and image process., 2003, pp. 8-11.
Sadeghi, S. et al. "Ultrasound elastography using empirical mode decomposition analysis." Journal of medical signals and sensors 4.1 (2014): 18.
Salisbury J. I. et al, "Using modern time series analysis techniques to predict ENSO events from the SOI time series," Nonlinear Processes in Geophysics, vol. 9, pp. 341-345, May-Jul. 2002.
Sandrin, L, et al. "Shear elasticity probe for soft tissues with 1-D transient elastography." IEEE transactions on ultrasonics, ferroelectrics, and frequency control 49.4 (2002): 436-446.
Sandrin, L. et al, "Transient elastography: a new noninvasive method for assessment of hepatic fibrosis," Ultrasound Med. Biol., vol. 29, pp. 1705-1713, Dec. 2003.
Sarvazyan, A.P. et al, "Shear wave elasticity imaging: a new ultrasonic technology of medical diagnostics," Ultrasound in medicine & biology, vol. 24, pp. 1419-1435, Nov. 1998.
Schiro, A. L. A research platform for ultrasonic elastograpy based targeted prostate biopsy. Diss. University of British Columbia, 2013.
Song, P. et al., in "Two-dimensional shear-wave elastography on conventional ultrasound scanners with time-aligned sequential tracking (TAST) and comb-push ultrasound shear elastography (CUSE)," IEEE Trans Ultrason Ferroelectr Freq Control., 2015; 62(2):290-302.
Song, P.F. et al, "Comb-Push Ultrasound Shear Elastography (CUSE): A Novel Method for Two-Dimensional Shear Elasticity Imaging of Soft Tissues," IEEE Trans. Med. Imag., vol. 31, pp. 1821-1832, Sep. 2012.
Wang X.J. et al, "Neurophysiological and Computational Principles of Cortical Rhythms in Cognition, " Physiological Rev., vol. 90, pp. 1195-1268, Jul. 2010.
Wang, M. et al, "Imaging transverse isotropic properties of muscle by monitoring acoustic radiation force induced shear waves using a 2-D matrix ultrasound array," IEEE Trans. Med. Imag., vol. 32, pp. 1671-1684, Sep. 2013.
Yamakoshi, Y. et al., "Ultrasonic imaging of internal vibration of soft tissue under forced vibration," IEEE Trans. Ultrason., Ferroelectr., Freq. Control, vol. 37, pp. 45-53, 1990.
Yin, M. et al, "Assessment of hepatic fibrosis with magnetic resonance elastography," Clinical Gastroenterology and Hepatology, vol. 5, pp. 1207-1213, Oct. 2007.
Zhao, H. et al, "External Vibration Multi-Directional Ultrasound Shearwave Elastography (EVMUSE): Application in Liver Fibrosis Staging," IEEE transactions on medical imaging, vol. 33, pp. 2140-2148, Nov. 2014.
Baghani, Ali, A High-Frame-Rate Ultrasound System for the Study of Tissue Motions, IEEETransactions on Ultrasonics, Ferroelectrics, and Frequency Control, vol. 57, No. 7, Jul. 2010, pp. 1535-1547.†
Schiro, Arthur Leland, A Research Platform for Ultrasonic Elastography Based Targeted ProstateBiopsy, Masters thesis submitted May 2013, made publicly available Nov. 30, 2013 by the Universityof British Columbia ciRcle system.†
Azar, Zahiri et al., 2-D High-Frame-Rate Dynamic Elastography Using Delay Compensated andAngularly Compounded Motion Vectors: Preliminary Results, IEEE Transactions on Ultrasonics, Ferroelectrics, and Frequency Control, vol. 57, No. 11, Nov. 2010, pp. 2421-2010.†
Eskandari, Hani, Identifying Malignant and Benign Breast Lesions Using Vibroelastography, Ultrasonics Symposium (IUS), 2013 IEEE International, pp. 25-28, IEEE, 2013.†

\* cited by examiner
† cited by third party

SYSTEMS AND METHODS FOR ULTRASOUND ELASTOGRAPHY WITH CONTINUOUS TRANSDUCER VIBRATION

CROSS-REFERENCE TO RELATED APPLICATIONS

This application is a U.S. 371 National Phase entry of PCT/US2016/055649, filed Oct. 6, 2016, which claims the benefit of U.S. Provisional Patent Application Ser. No. 62/238,891, filed on Oct. 8, 2015, and entitled "SYSTEMS AND METHODS FOR ULTRASOUND ELASTOGRAPHY WITH CONTINUOUS TRANSDUCER VIBRATION."

STATEMENT REGARDING FEDERALLY SPONSORED RESEARCH

This invention was made with government support under DK106957 awarded by the National Institutes of Health. The government has certain rights in the invention.

BACKGROUND OF THE INVENTION

The field of the invention is systems and methods for ultrasound elastography. More particularly, the invention relates to systems and methods for processing data acquired using ultrasound elastography.

Ultrasound shear wave elastography ("SWE") has emerged as a new ultrasound imaging technique that can noninvasively and quantitatively assess tissue mechanical properties, which are strong biomarkers for the state of tissue health. Typically, in SWE shear waves are induced in tissues and the propagation of the shear waves is detected with pulse-echo ultrasound. The detection of the shear waves is then used to calculate parameters related to tissue mechanical properties, including shear wave propagation speed, dispersion (i.e., frequency dependency), shear wave attenuation, shear modulus, shear viscosity, Young's modulus, storage modulus, loss modulus, loss tangent, and mechanical relaxation time.

Conventional ultrasound SWE uses an acoustic radiation force ("ARF") to generate shear waves in the tissue. ARF requires transmission of long-duration push pulses from the ultrasound transducer, which demands a long period of cooling time before the next transmission to avoid potential probe and tissue heating. This fundamentally limits the frame rate of ultrasound SWE (e.g., to about 1 Hz). ARF also has high power supply requirements to the ultrasound system, which makes it challenging to be implemented in mid and low-end ultrasound scanners.

To address these limitations, an ultrasound elastography technique with continuous vibration of the ultrasound transducer the techniques described in U.S. Provisional Application Ser. No. 62/072,167). This technique generates shear waves through continuous vibration of the transducer, and detects the generated shear wave signal with the same transducer. Because this technique does not use ARF for shear wave generation, it allows for continuous high frame-rate shear wave imaging and convenient implementation with mid and low-end ultrasound systems.

The continuous vibration of the transducer, however, also introduces challenges for shear wave signal processing. One major challenge is correcting the acquired data for motion of the transducer, and another major challenge is motion signal alignment when imaging with a line-by-line scanning ultrasound system.

SUMMARY OF THE INVENTION

The present invention overcomes the aforementioned drawbacks by providing a method for measuring a mechanical property of an object using an ultrasound system having a transducer. A continuous vibration is provided to the ultrasound transducer, whereby vibration of the ultrasound transducer induces at least one shear wave in the object. Motion data are then acquired from the object using the ultrasound transducer. The motion data are indicative of the at least one shear wave propagating within the object. A compression profile that is indicative of a deformation of the object caused by the continuous vibration of the ultrasound transducer is then estimated and used to produce corrected data by demodulating, separating, or otherwise removing the compression profile from the acquired motion data. The corrected data are then processed to calculate a mechanical property of the object.

It is another aspect of the invention to provide a method for measuring a mechanical property of an object using an ultrasound system having a transducer. A continuous and periodic vibration is provided to the ultrasound transducer, whereby vibration of the ultrasound transducer induces at least one shear wave in the object. Motion data are then acquired from the object using the ultrasound transducer. The motion data are indicative of the at least one shear wave propagating within the object, and are acquired at time points selected to mitigate motion errors attributable to deformations in the object caused by the continuous and periodic vibration. The motion data are then processed to calculate a mechanical property of the object.

It is another aspect of the invention to provide a method for measuring a mechanical property of an object using an ultrasound system having a transducer. Shear waves are induced in an object and motion data are acquired from the object using an ultrasound transducer in a pulse-echo mode. The motion data are indicative of the shear waves propagating within the object. The motion data are then corrected for errors caused by time delays between data acquisitions at different locations in the object, and the corrected data are processed to calculate a mechanical property of the object.

The foregoing and other aspects and advantages of the invention will appear from the following description. In the description, reference is made to the accompanying drawings that form a part hereof and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Described here are systems and methods for processing data acquired using ultrasound elastography, in which shear waves are generated in a subject using continuous vibration of the ultrasound transducer. The systems and methods described here can effectively remove motion artifacts associated with vibration of the ultrasound transducer, and can also remove the data sampling misalignment caused when a line-by-line imaging mode is used to acquire data, as is done by many conventional ultrasound scanners.

Thus, the systems and methods described here provide techniques for transducer motion correction and for aligning motion signals detected by line-by-line scanning ultrasound systems.

Figure 1:
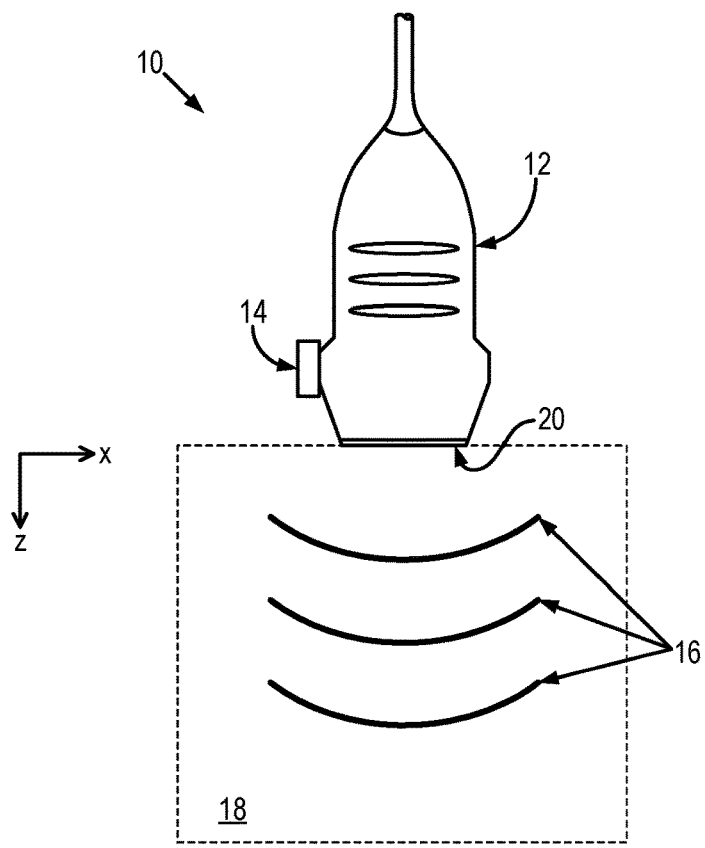
FIG. 1 is a block diagram of an example ultrasound system that implements a continuous vibration of the ultrasound transducer to induce shear waves in an object.

Referring first to FIG. 1, an example system 10 for inducing shear waves in an object 20 is illustrated. In this system, the transducer 12 is mechanically vibrated by an actuator 14, which causes the transducer 12 to oscillate in the axial direction (e.g., the z-direction in FIG. 1). As one example, the actuator 14 can be a mechanical actuator, such as a voice coil actuator. As the transducer 12 moves in the axial direction, shear waves 16 are induced within the object 18. Shear waves 16 can also be produced from mode conversion of compressional waves. The produced shear waves 16 are then detected by the same ultrasound transducer 12 operating in a pulse-echo mode to provide quantitative measurements of mechanical properties of the object.

The actuator 14 is coupled to the ultrasound transducer 12. As one example, the actuator 14 can be attached directly to the outer surface of the transducer 12. For illustration purposes, the actuator 14 is attached to one side of transducer 12 in FIG. 1. In some applications, however, it may be preferred to align the actuator co-axially with the transducer 12 so that the transducer motion is primarily axial with minimal transverse and azimuthal motions. This setup eliminates the need for a separate vibration source, and therefore allows for a convenient single-handed operation. The vibration is preferably continuous to allow continuous updating of measurements.

The ultrasound transducer 12 can be vibrated axially along the beam axis of ultrasound, or in other directions depending on the desired imaging application. The ultrasound system used for shear wave detection can be operated to detect a single A-line, multiple A-lines through parallel beam forming, or an entire 2D area or 3D volume with plane wave imaging and software beam forming, such as is done in a Verasonics® ultrasound scanner.

The continuous vibration applied to the ultrasound transducer 12 by the actuator 14 can contain multiple frequencies, and the detected shear waves can thus be processed to resolve frequency dependent properties of the object. For example, the processing may use a bandpass filter along the time dimension to select only one frequency at a time, and the subsequent processing would be identical to that as if data were collected with a single vibration frequency. Multi-frequency vibrations can speed up acquisition for dispersion analysis. With continuous vibration and continuous shear wave detection and processing, elastography measurements can be updated continuously in a substantially real-time manner.

When the transducer 12 is vibrating in the axial direction, such as when the vibration is normal to the active surface 20 of the transducer 12, the motion of the transducer 12 will contaminate the shear wave signals detected in the object 18. This signal contamination is present because ultrasound motion detection uses the transducer 12 as a non-moving reference coordinate, but this assumption is violated when the transducer 12 is oscillating due to external vibration. Therefore, motion of the transducer 12 that is caused by the actuator 14 needs to be corrected for in order to properly measure mechanical properties from the detected shear waves.

Transducer Motion Correction

In one aspect of the disclosure, systems and methods for correcting transducer motion during continuous transducer vibration are provided. In ultrasound, measurements of tissue motion are made by comparing the time shift, τ, of ultrasound echo signals between two pulse-echo events. Because the ultrasound propagation speed, c, in soft tissues is a constant (commonly assumed to be c=1540 m/s), this time shift can be converted to tissue displacement as, $$d = \frac{c\tau}{2}; \qquad (1)$$

where the factor of two accounts for round trip distance in pulse-echo ultrasound detection. The mean tissue particle velocity, v, can also be calculated by, $$v = \frac{d}{\delta}; \qquad (2)$$

where δ is the time interval between the two pulse-echo events. Sometimes, compounding from multiple pulse-echo events is used to form a single set of echoes to improve signal-to-noise ratio ("SNR"). In such situations, compounded pulse-echo events may each be composed of multiple transmit-receive processes. As used herein, the term "motion" can include displacement, velocity, acceleration, and so on.

As illustrated below in FIGS. 2A-2C, and as described above, motion detection in ultrasound uses the ultrasound transducer as the reference coordinate. When vibrating the transducer itself in continuous transducer vibration, however, the transducer is in motion to produce shear waves. This has several effects. First, the reference coordinate of motion detection is moving, which adds a constant motion offset to all imaged pixels or voxels at a given time instant. Second, the transducer physically pushes on the tissue and causes a compressional deformation in the tissue. Tissue motion due to this effect changes with the location of each imaged pixel or voxel, even at the same time instance. Third, the vibrating transducer produces shear waves in tissue, which is the signal that is used to estimate tissue mechanical properties. Therefore, it is important to remove motions due to the first two effects in order to recover motions due to shear waves for accurate calculation of tissue mechanical properties.

Figure 2A:
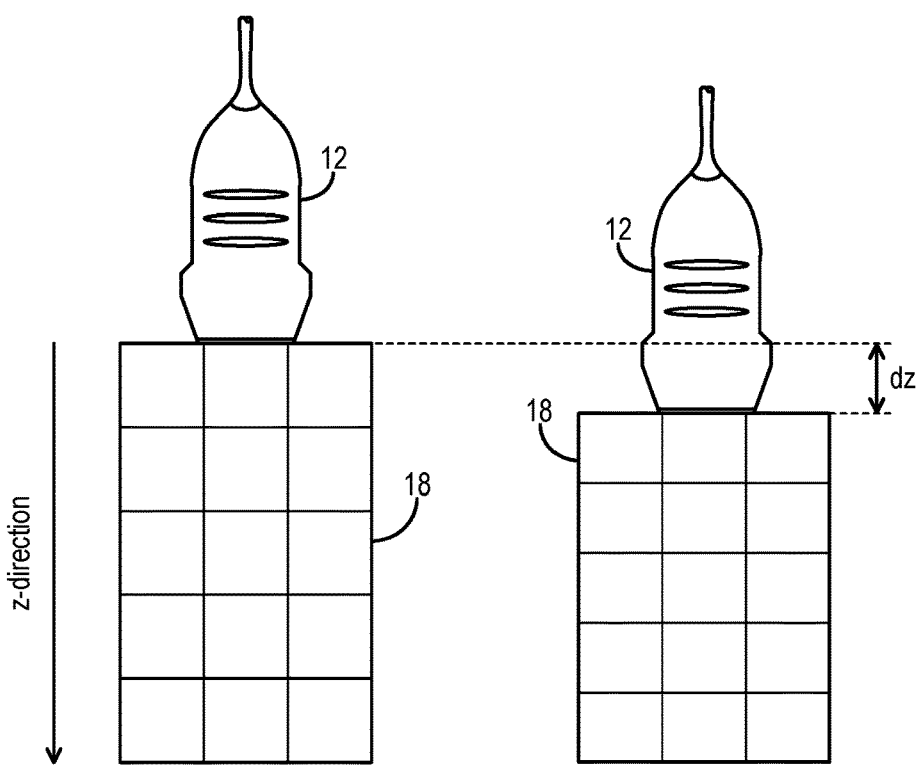
FIGS. 2A-2C illustrate examples of inducing shear waves and additional deformations in an object using continuous vibration of an ultrasound transducer.
Figure 2B:
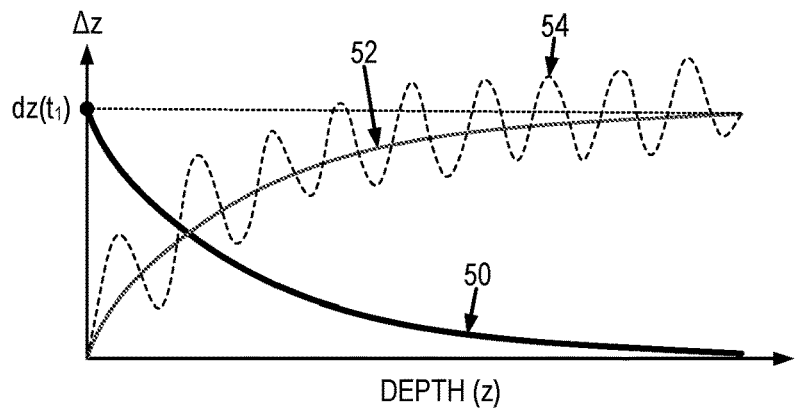

FIG. 2A shows illustrates a uniform compression, dz, applied by an ultrasound transducer 12 at the top surface of a tissue object 18. The displacement resulting from the deformation of the tissue is dependent on both position and material properties of tissue. As an example, the black line 50 in FIG. 2B shows the change in displacement along the depth (e.g., z-direction) after compression by the continuously vibrating transducer at a time point, $t_1$. The displacement is measured at a stationary reference point set at the top of the uncompressed object. Tissue compression measured by the transducer is shown as the solid grey line 52 in FIG. 2B, because the transducer surface is used as a reference coordinate here. The total tissue motion measured by the transducer, including deformation due to compression and shear waves caused by the transducer vibration, is illustrated as the dashed line 54 in FIG. 2B.

Figure 2C:
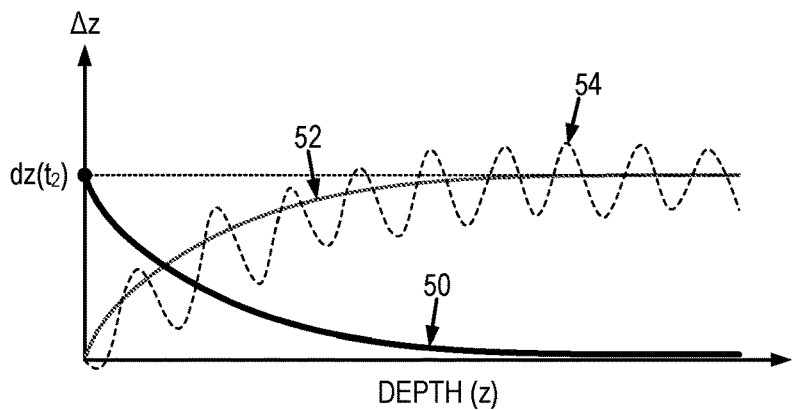

The deformation and shear wave motion at a second time point, $t_2$, are shown at FIG. 2C. In this example illustrated in FIG. 2C, the deformation 52 due to transducer compression is smaller (i.e., there is a smaller dz) and the shear wave has propagated through the medium, noted by the phase shift along the z-direction for the total motion signal 54.

Figure 3:
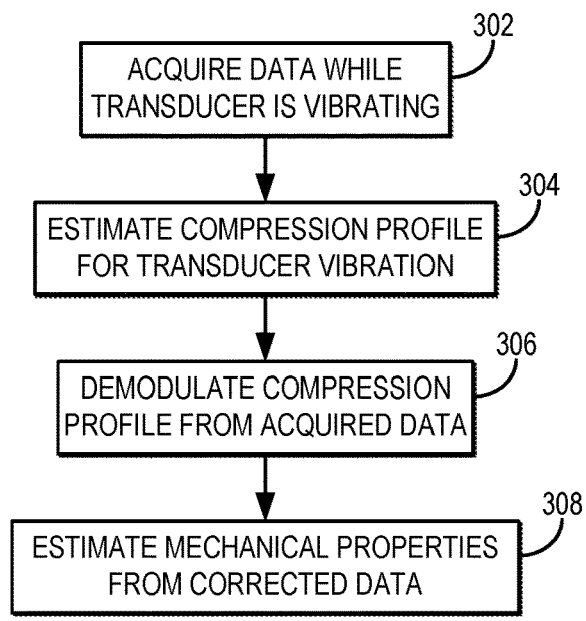
FIG. 3 is a flowchart setting forth the steps of an example method for acquiring motion data in response to a continuously vibrating ultrasound transducer and correcting the acquired data for effects of the transducer vibration.

Referring now to FIG. 3, flowchart is illustrated as setting forth the steps of an example method for correcting transducer motion during continuous transducer vibration. The method generally includes acquiring data from an object using a transducer that is vibrating to generate shear waves in the object awhile the data are being acquired from the object, as indicated at step 302. The acquired data indicate the total, observed motion in the object. After the data are acquired, a compression, or deformation, profile representative of the transducer vibration during data acquisition is estimated, as indicated at step 304. The compression profile can be estimated according to a number of different procedures, which are described below in more detail. Using the estimated compression profile, the effects of transducer motion are demodulated, separated, or otherwise removed from the acquired data, as indicated at step 306. As one example, the transducer motion can be removed from the data by subtracting the compression profile from the acquired data. From the corrected data, mechanical properties of the object can be estimated, as indicated at step 308.

Estimating the Compression Profile Using Curve Fitting

As one example method for estimating the compression profile, a curve fitting procedure can be implemented. In this approach, the compression profile can be estimated by fitting the total motion (depicted as the dashed line in FIG. 2B) to a known function. As an example, the known function can include one or more of the following: an exponential, a polynomial, a power law, a spline, a Flamant solution, and a Boussinesq solution. In some embodiments, to account for local changes in material properties, multiple functions can be used to estimate the compression profile in multiple spatial windows at different depths. The spatial window can be a one-dimensional, two-dimensional, or three-dimensional window.

To improve the estimation of the compression profile, the measured total motion can be denoised prior to the curve-fitting procedure. As an example, denoising can be implemented using filtering or regularization methods.

The methods described here can be extended to higher-dimensional images using various approached, in one example, the previously described fitting methods can be extended to multi-dimensional counterparts allowing for axial, lateral, and temporal estimation of the compression to be conducted for one or more frames. The term "frame" can refer to a two-dimensional ("2D") ultrasound echo data set obtained at a given time, and multiple frames can be obtained at the same 2D plane over time. In another example, the fit is performed along a single 1D profile repeated at each lateral position, which allows for removing the effects of the transducer motion from the entire imaged frame. In other implementations, a single deformation profile can be applied to each lateral position within the image in order to further reduce the computational time. This process can also be repeated on each frame of an acquisition (i.e., applied to different time instances) to correct transducer motion from the entire acquisition over time.

In the curve-fitting example described above, transducer motion is estimated along the compression direction from a single lateral location and a single frame. Like any acquisition technique, all measurements will contain some error. As such, utilizing information from multiple spatial locations and multiple frames will reduce random errors and provide better estimates of the true compression profile. This can be done in at least two ways.

In one method, multiple total observed motion signals measured at several adjacent lateral positions are combined using a mean, weighted mean, median, or similar technique in order to obtain a less noisy total motion measurement for curve fitting and subtraction.

In another method, the compression profile from each frame is estimated, the estimated profiles are combined into a single compression profile, and the combined profile is subtracted from each frame to remove compression effects. While each frame will be acquired at a different time point, and will compress the tissue to different degrees, it can be assumed, as a first-order approximation, that the compression profiles will be amplitude scaled versions of one another.

Thus, it is possible to normalize all of the individual compression profiles of different frames at each lateral location such that the profiles will be combined (such as using averaging) into a single compression profile for each lateral location where random noise is suppressed. The combined compression profile can be scaled by, and fit to, individual frames and then subtracted to obtain the true shear wave motion at that lateral position. The same process can be repeated for all lateral positions to obtain shear wave signals over a 2D area for further processing. Note that these two techniques are not mutually exclusive and can be used in conjunction with one another.

Estimating the Compression Profile Using Reference Data

As another example method for estimating the compression profile, a reference compression profile can be obtained and implemented. In this approach, a quasi-static compression is applied to the object and a reference compression profile is estimated by pulse-echo detection using the same ultrasound transducer. The quasi-static compression can be achieved with manual compression or by vibrating the transducer at a frequency much lower than that typically used in shear wave imaging (e.g., 1 Hz).

It can be assumed that motions due to shear waves are negligible in this situation; thus, the measured motion profile should be due only to transducer compression. As a first-order approximation, compression profiles at different compression levels, dz, should be scaled versions of each other. Thus, one reference compression profile obtained at a single compression level should be sufficient. Alternatively, multiple compression profiles can be obtained at different compression levels, and can be scaled and combined to form a single reference compression profile with a higher signal-to-noise ratio ("SNR") using similar processes as those described above with respect to combining compression profiles for curve fitting.

The reference compression profile can be scaled, fit to the measured total tissue motion, and subtracted from the total tissue motion to obtain the true shear wave motion. The spatial and temporal averaging techniques described above with respect to curve fitting can also be used in the reference compression method to improve SNR.

Estimating the Compression Profile Using a Computational Model

As another example method for estimating the compression profile, a compression profile modeling can be implemented. In this approach, the compression profile can be obtained from finite element method ("FEM") simulation or analytical solutions. Once the modeled compression profile is known, it can be scaled, fit, and subtracted from the measured total tissue motion as described above. As a first approximation, the object can be assumed to be homogeneous. For a homogenous medium, the compression profile from a flat surface transducer should not change with the shear modulus of the medium. Therefore, a typical shear modulus, such as 1 kPa, can be used for such modeling. For objects containing heterogeneous materials or tissues, compression profiles from homogeneous assumptions can be used to obtain the first order solution of the 2D elasticity image of the object. This image can then be used to run another FEM simulation to obtain a more accurate compression profile for better reconstruction of the true 2D elasticity image of the object.

Estimating the Compression Profile Using Adaptive Estimation

As another example method for estimating the compression profile, an adaptive estimation method can be implemented. In this approach, the compression profile can be estimated by applying spatial mean, weighted mean, median or similar techniques to the measured total motion in a series of small spatial windows along the depth axis (i.e., the z-axis). The spatial window can be a one-dimensional, two-dimensional, or three-dimensional window. It is contemplated that shear waves will be cyclic over the depth direction and will diminish when applying the averaging process. Thus, after the averaging process it is contemplated that the compression profile will remain. Similar to the curve fitting method described above, these adaptive methods can incorporate information from multiple spatial locations and temporal instances to increase the accuracy and precision of the estimated compression profile. This can be done by applying either multidimensional convolution techniques with specialized kernels, such as Gaussian or Laplacian kernels, or other multidimensional filters, such as median or bilateral filters.

Removing the Compression Profile in k-Space

In some situations it is not necessary to estimate the compression, but instead the compression can be directly decoupled from the shear waves. If multiple frames are acquired across the full motion path of the transducer, such that motion is obtained in both the depth direction (e.g., z-direction) and lateral direction x-direction) at multiple time points (e.g., frames), the propagating shear wave signal can be separated from the compression. This can be done by utilizing the differences in the k-space representation of propagating waves and non-propagating motion.

Figure 9:
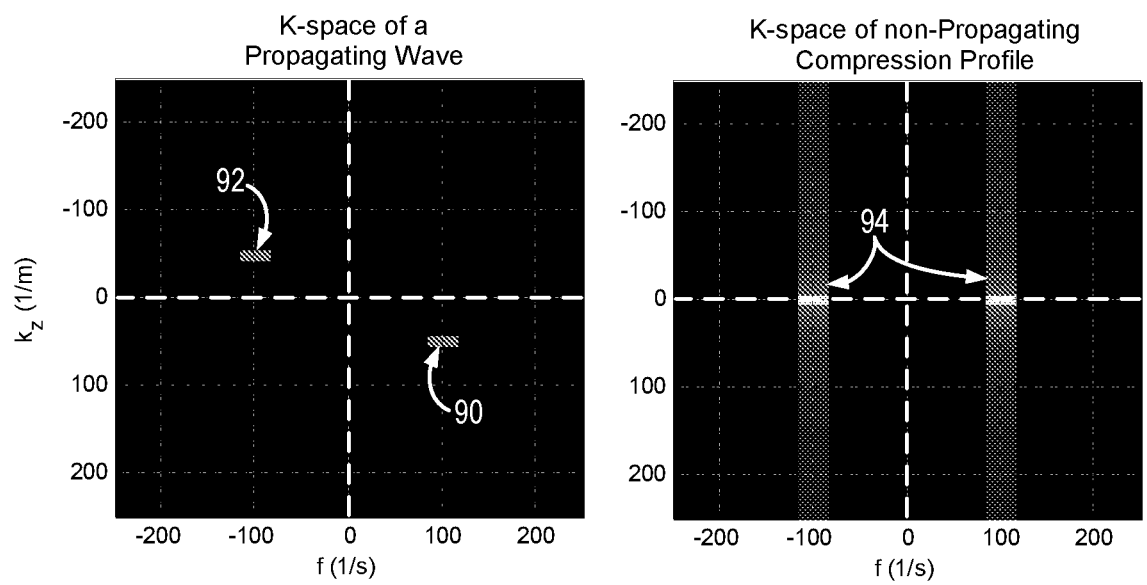
FIG. 9 depicts a k-space representation of propagating shear waves and a non-propagating compression profile.

As shown in FIG. 9, for a wave propagating in the depth direction (e.g., the z-axis), the spectral representation in the k-space $k_z$-f plane (where $k_z$ denotes the wavenumber in the depth direction and f denotes the temporal frequency) will contain two conjugate symmetric peaks 90, 92. The first peak 90 is located at the point corresponding to the positive wavenumber and temporal frequency of the signal, and the second peak 92 is radially symmetric to the first and is located at the point corresponding to the negative wavenumber and negative temporal frequency. Thus, the k-space representation of the propagating signal will occur in non-adjacent quadrants of the $k_z$-f plane, and is not conjugate symmetric across the $k_z$-axis. Given that, as a first-order approximation, the compression profile will be amplitude scaled, but non-propagating, the spectral information 94 associated with the compression profile in k-space will be conjugate symmetric across the $k_z$-axis. A representation of the k-space for a propagating wave and non-propagating compression is shown in FIG. 9.

Because the compression profile is conjugate symmetric across the $k_z$-axis, while the propagating waves do not share this same property, the shear waves can be decoupled from the compression by utilizing this difference in symmetry. One method to accomplish this is to represent each point in k-space as $k(f_M, k_{zN})$, where $f_M$ and $k_{zN}$ represent one of the temporal frequencies and wavenumber pairs defining a single point in k-space. The complex conjugate of $k(f_M, -k_{zN})$ can be added to all points, $k(f_M, k_{zN})$, defined in k-space, and the shear wave motion can then be recovered by applying the inverse Fourier transform on the k-space data. To restore the wave propagation the quadrants that did not originally contain the shear wave signal can be attenuated or set to zero before applying the inverse Fourier transform. While this method was described here for waves propagating in 1D space and 1D time, it will be appreciated by those skilled in the art that this method can be readily extended to 2D space, 3D space, and so on.

Estimating the Compression Profile from k-Space

As another example method for estimating the compression profile, the compression profile can be estimated from k-space. In this approach, a Fourier transform is applied along the depth direction (e.g., the z-axis) of the observed signal, u(z), at a given frame to obtain the frequency domain representation $U(k_z)$. This frequency domain representation can be referred to as k-space. For a given pixel in k-space with coordinate $k_z$, the distance to the origin of k-space is representative of the spatial frequency of that pixel.

It can be assumed that the compression profile is slowly increasing and smooth. Thus, the deformation signal in k-space will also retain smoothness. However, the k-space components of the shear wave will be at distinct points in k-space corresponding to the wavelength in image space. This results in increased amplitudes at one or more values of $k_z$ associated with the frequencies of those shear wave components. When the k-space combined spectrum of the compression and shear wave signals are evaluated together, the spectrum will be smoothly varying with one or more amplitude discontinuities due to the shear wave motion signal. By removing the k-space components corresponding to the shear wave signal through the use of mean, weighted mean, median, or other filtering methods, an estimate of the frequency components corresponding to the compression profile can be obtained. The estimated compression profile can be produced by performing an inverse Fourier transform to convert the k-space signal back to image space. The spatial averaging or frame averaging approaches described above can be used to improve the SNR of the compression profile estimation. Alternatively, this method can be extended to higher dimensions when using 2D/3D spatial region and/or including temporal dimension by using multiple frames.

Figure 4A:
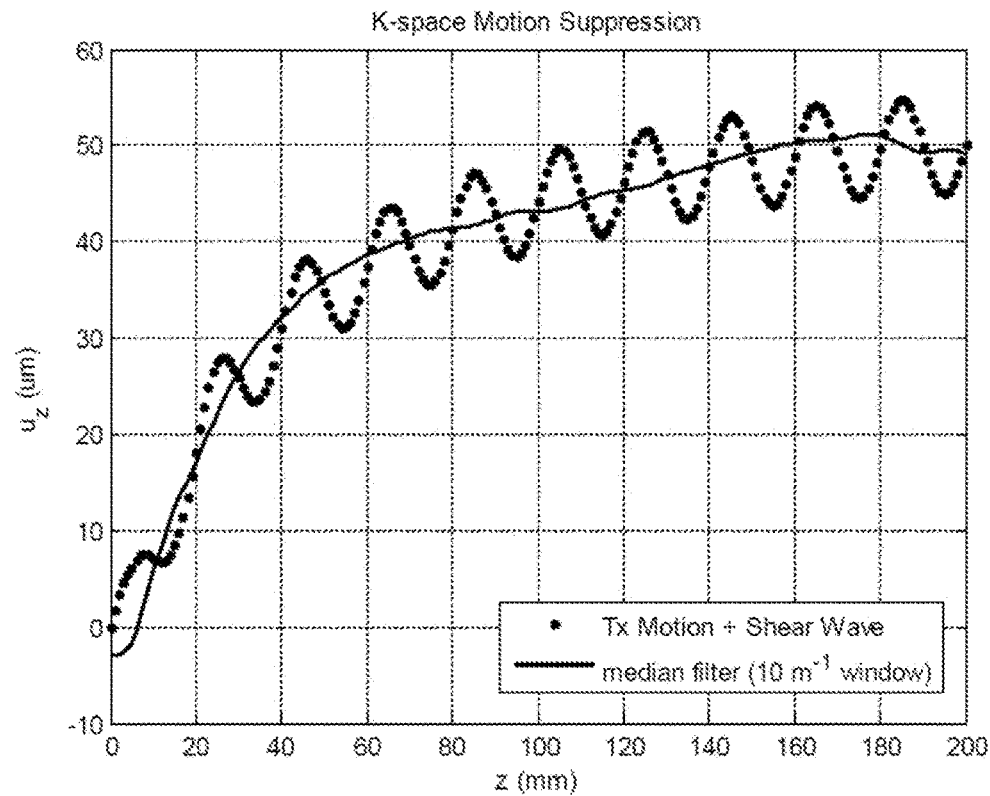
FIGS. 4A-4B illustrate examples of estimating a compression profile from k-space data generated from acquired motion data.
Figure 4B:
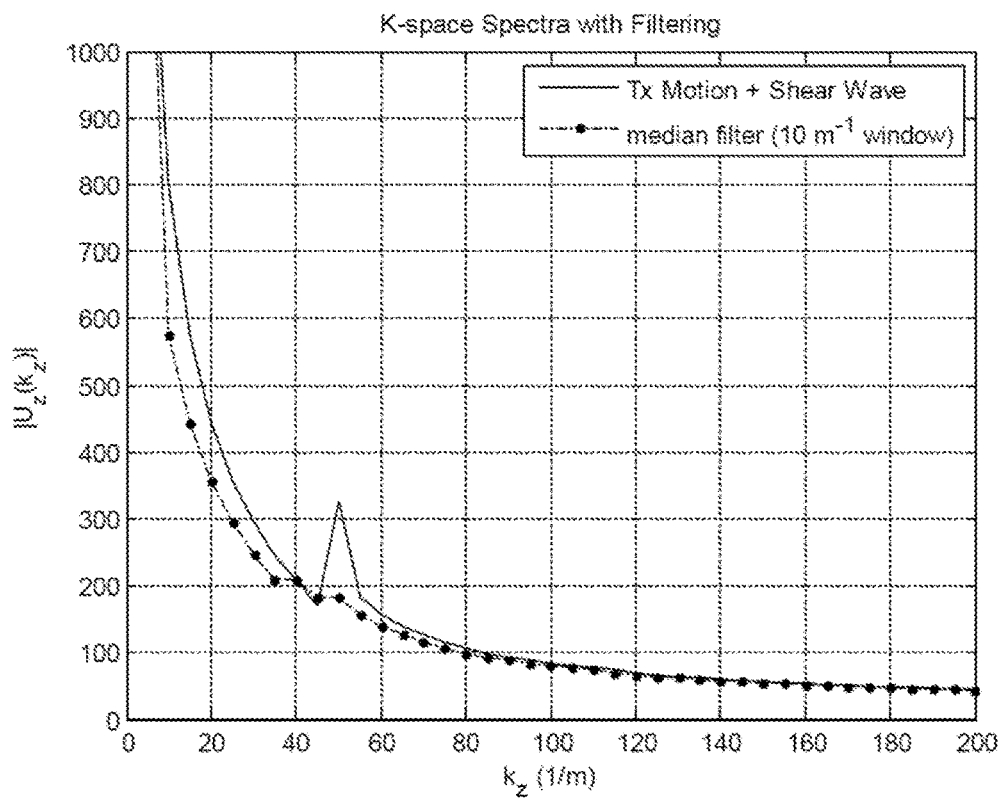

This process is generally illustrated in FIG. 4A, where a sinusoidal shear wave signal has been added to a compression profile simulated using a FEN simulation of an elastic material (black dots). Using the Fourier transform to convert to k-space, the resulting spectrum has a single frequency component corresponding to the shear wave at 50 m$^{-1}$ (FIG. 4B, solid line). Applying a sliding median filter with 10 m$^{-1}$ sliding window (applied from 10-200 m$^{-1}$) leads to the filtered spectra (FIG. 4B, dashed with dots). The filtered spectrum has no peak corresponding to the shear wave signal, and when transformed back to image space provides an estimate of the compression profile due to transducer motion (FIG. 4A, solid line).

Ultrasound Detection at Peaks or Valleys of Sine Wave

In some embodiments, the compression profile is not estimated, but rather the data acquisition is altered to minimize the effects of the transducer motion. Particularly, for a transducer vibrating sinusoidally, pulse-echo detection made at time instances near the peaks or valleys of the sine signal may suppress tissue deformation due to the transducer compression.

Figure 5:
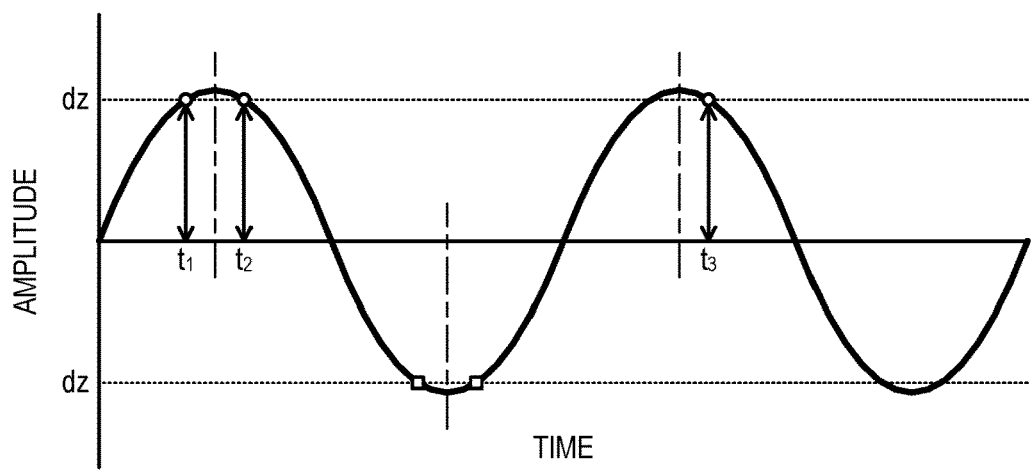
FIG. 5 illustrated an example of implementing pulse-echo motion detection near peaks (circles) and valleys (squares) of a sine signal representative of a continuous transducer vibration.

As shown in FIG. 5, when the two pulse echo events of motion detection are made at times $t_1$ and $t_2$ symmetric to the peak of the sine wave (i.e., the time from $t_1$ to the peak of the sine wave is equal to the time from the peak of the sine wave to $t_2$), the transducer will be at the same compression position, dz, at both times $t_1$ and $t_2$. By acquiring data at these times, tissue deformation is not detected because the pulse-echo only detects relative motion between times $t_1$ and $t_2$. As a result, only propagating shear waves are detected using this acquisition.

Similarly, detection at valleys of the sine wave (the squares in FIG. 5) can also be implemented to suppress tissue deformation due to transducer compression. The method is valid for different time intervals between the pulse echo events, as long as they are placed symmetric to the peak or valley of the sine wave. However, because the detected motion is an averaged motion between these two pulse echo events, the time interval, $\Delta t = t_2 - t_1$, should not be too large in order to provide sufficient time resolution for shear wave detection. Note that the sine signal is periodic; therefore, detection events at one or more whole cycles apart from $t_2$, such as $t_3$ in FIG. 5, are identical to the detection event at $t_2$. This allows more flexibility in pulse-echo timing.

In the cases where detections do not occur when the transducer is at the same position, it is possible to obtain an image with the effects of transducer motion minimized. This can be done by utilizing other detections to recover or estimate the motion when the detections were symmetric about the peak or valley of the motion profile. This can be performed using interpolation, parametric fitting, or phase shifting methods.

Using a Motion Sensor to Measure Transducer Motion

As another example method for estimating the compression profile, the compression profile can be estimated from data acquired with motion sensors that are coupled to or integrated with the ultrasound transducer. In this approach, motion sensors for measuring acceleration, velocity, displacement, and so on can be coupled to or integrated within the ultrasound transducer to measure its vibration. This approach provides certain additional advantages. As one example, the vibration response of the transducer may have a phase delay compared to the sine signal that is used to drive the actuator that vibrates the transducer. In these instances, a sensor measuring the motion of the transducer can provide accurate synchronization for ultrasound detection at the peaks or valleys of the sine wave as described above. As another example, the transducer motion measured by motion sensors may be used to properly scale the deformation profiles in the motion subtraction methods described above. Thus, it is contemplated that using motion sensors to measure the motion of the transducer can be used alone or in combination with the methods described above.

As an alternative to using a motion sensor, the motion of a stationary target detected by the moving transducer can also be used to estimate the position of the transducer, and to improve the accuracy of synchronization for ultrasound detection at the peaks or valleys of the sine wave as described above. As an example, the stationary target can be a non-moving bone or a tissue target at a deep position (where shear waves are fully attenuated) in the field of view of the transducer.

Correction of Time Delay in Ultrasound Motion Detection

In another aspect of the disclosure, systems and methods for correcting time delays in ultrasound motion detection are provided. After shear waves are generated in tissues, the shear waves can be detected using pulse-echo motion detection, as described above. To produce a 2D image of mechanical properties of tissue, simultaneous detection of tissue motion over a large 2D area with high temporal resolution is desired. This can be achieved by "plane wave" imagers, where echoes from every pixel within the 2D detection area can be reconstructed from a single transmission of a plane ultrasound wave.

However, most commercial ultrasound scanners do not use plane wave imaging, but instead still use a sequential line-by-line scanning approach, where multiple pulse-echo events are required to cover a 2D detection area. Line-by-line scanners thus have a significantly lower imaging frame rate than plane wave imagers. In addition, with line-by-line scanners, the time delay between each imaging line within the 2D imaging area needs to be accounted for in order to correctly calculate the mechanical properties of tissues from detected shear waves. Several techniques for addressing this challenge for detecting shear waves with line-by-line scanners are described below.

Figure 6:
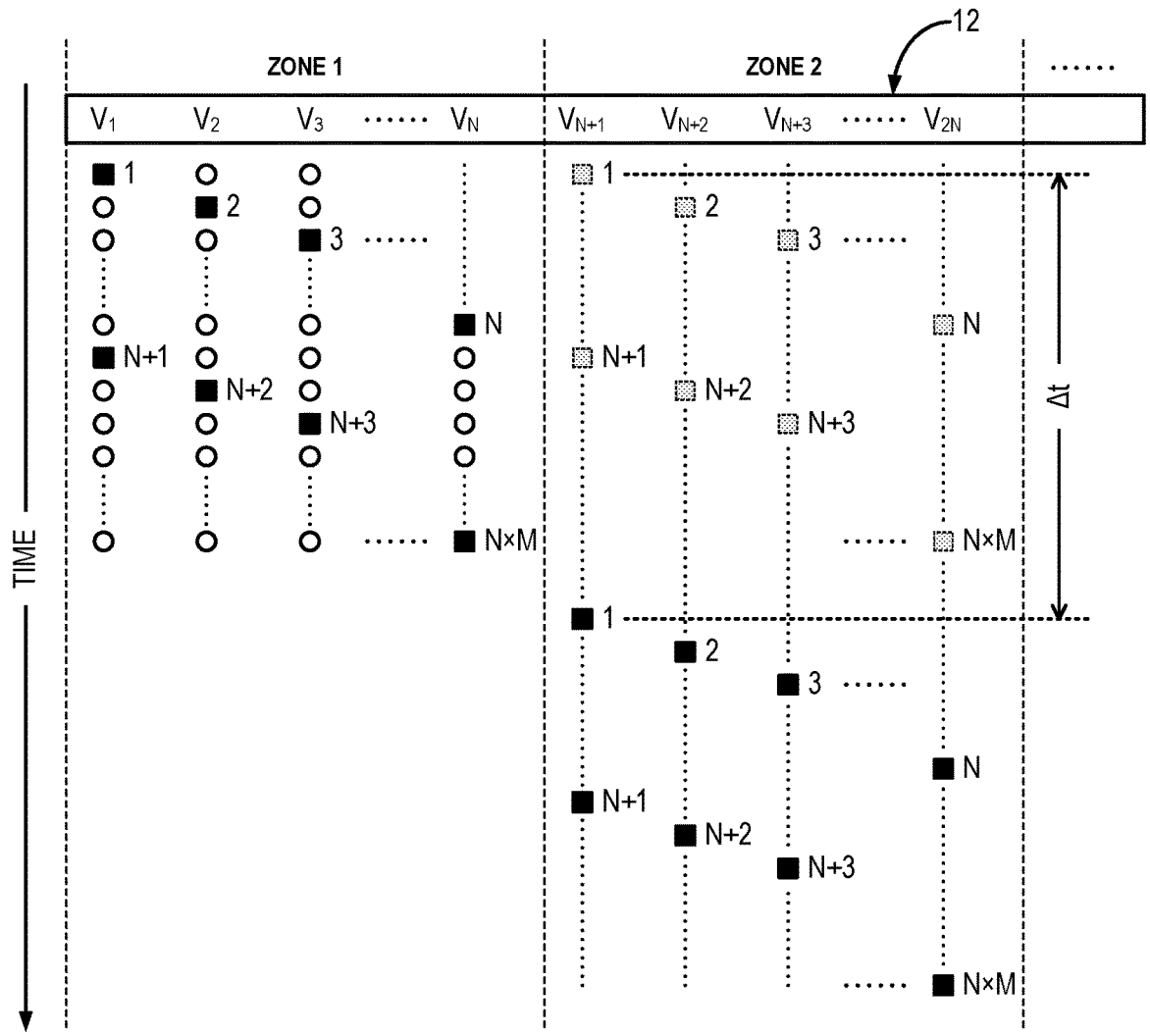
FIG. 6 illustrates a schematic plot of motion signal alignment methods. The time alignment of motion detection is illustrated within zone 1. The proposed zone-to-zone alignment method is depicted for zone 2. The solid squares indicate the actual pulse echo events. The hollow circles indicate data points interpolated in time. The gray squares with dashed outlines indicate time-shifted motion signal data points based on the zone-to-zone alignment.

As shown in FIG. 6, a transducer 12 implemented in a line-by-line scanner can be operated to sequentially and periodically fire detection beams in a first zone of the transducer 12 (e.g., zone 1) following an order.

$V_1 \rightarrow V_2 \rightarrow V_3 \rightarrow \ldots V_N \rightarrow V_1 \rightarrow V_2 \rightarrow \ldots V_N$ where V is the imaging vector each containing n imaging A-lines that can be parallel beamformed during one pulse-echo event; N is the total number of imaging vectors within each imaging zone; and M is the number of pulse-echo events acquired at each imaging vector position. The solid black squares in FIG. 6 represent the time instances of pulse-echo events, and the number next to each black square indicates the time sequence of each pulse-echo event.

Assuming that the pulse repetition frequency for the pulse-echo events is $PRF_0$, then the upper limit of $PRF_0$ is controlled by the imaging depth. The effective pulse repetition frequency at each vector is, $$PRF_e = \frac{PRF_0}{N}; \quad (3)$$

It is often desirable to maintain a high $PRF_e$, such as 1 kHz; therefore, N should be small enough to sustain a high $PRF_e$. Reducing the number of imaging vectors, however, will reduce the size of each zone; thus, with smaller values of N, multiple zones may be required to cover a large 2D detection area.

As shown in FIG. 6, the sequential tracking proceeds to another zone (e.g., zone 2) of the transducer 12 after all of the M samples have been collected for each vector in the preceding zone (e.g., zone 1). The same tracking sequence is repeated until all of the M samples have been collected for each vector in zone 2. Detection events for zone 2 are also represented by the black solid squares under zone 2. This process can be repeated until data in all zones are collected.

There are two problems with motion signals detected using the sequential tracking method as shown in FIG. 6. First, the detection events are not aligned in time within each zone. Second, there is a time delay, $$\Delta t = \frac{N \cdot M}{PRF_0}; \quad (4)$$

between temporally adjacent zones (e.g., zone 1 and zone 2). As explained above, proper calculation of tissue mechanical properties requires that motion signals over the entire 2D imaging area should have the same time grid (i.e., should be time aligned).

Methods for aligning shear wave signals within each zone, such as the time interpolation described in co-pending U.S. Provisional Patent Application Ser. No. 62/072,167, can be used to correct for non-aligned motion signals. In time interpolation, echoes from each vector over different pulse-echo events are first used to calculate tissue motion, which includes motion due to shear waves and deformation from transducer compression. Therefore, in time interpolation techniques, tissue motion is measured at the black solid squares. Interpolation in time at each vector position (indicated as white circles in zone 1 of FIG. 6) can align tissue motion signal within each zone.

Motion Signed Alignment: Phase Shift Signed to a Common Time Grid

As one example, motion signals can be aligned to a common time grid by applying appropriate phase shifts to the misaligned motion signals. Because tissue motion is a sine wave of known frequency, it allows additional methods to align the motion signal. Assume tissue motion, detected by vector $V_1$ in zone 1 as, $$M_1(t) = D_1 \cdot e^{j\omega t} \quad (5);$$

where $D_1$ is the motion amplitude at vector $V_1$, and $\omega$ is the frequency of continuous vibration from the ultrasound transducer. The tissue motion detected by vector $V_{N+1}$ in zone 2 will be, $$M_{N+1}(t) = D_{N+1} \cdot e^{j\omega\left(t + \frac{N \cdot M}{PRF_0}\right)}; \quad (6)$$

where $D_{N+1}$ is the motion amplitude at vector $V_{N+1}$, and $(N \cdot M)/PRF_0$ is the time delay between vector $V_1$ and $V_{N+1}$. A phase shift of $\exp(j\omega((N \cdot M)/PRF_0))$ can be applied to the signal in Eqn. (6) so that the time is aligned with that in Eqn. (5), $$D_{N+1} \cdot e^{j\omega\left(t + \frac{N \cdot M}{PRF_0}\right)} \cdot e^{-j\omega\left(\frac{N \cdot M}{PRF_0}\right)} = D_{N+1} \cdot e^{j\omega t}. \quad (7)$$

This phase shift method can be used to align vectors within each zone, and to align vectors across zones.

An example of the zone-to-zone time alignment method described above is shown in FIG. 7. In this example, a 50 Hz continuous vibration was used to produce continuous shear waves inside a tissue-mimicking homogeneous phantom. The $PRF_e$ for shear wave detection was 500 Hz, the parallel beamforming capability was 4, total number of imaging vectors was 64, the number of imaging zones was 2, and the number of temporal samples for each vector was 24. Before alignment, the zone-to-zone discontinuity of the shear wave signal along the lateral dimension can be seen. After within-zone alignment by time interpolation, the sequential tracking delay within each imaging zone was corrected, as can be seen by careful observations of the slope of the shear wave signal. However, the zone-to-zone discontinuity still exists, as predicted in Eqn. (6). After zone-to-zone time alignment, it can be seen that the zone-to-zone discontinuity was successfully removed (i.e., a continuous vibration can be clearly appreciated across different imaging zones).

Motion Signal Alignment: Parametric Fitting

As another example of aligning motion signals, the detected tissue motion at a given pixel over multiple time points (frames) can be fit to a sine time function to estimate the amplitude and phase of the sine wave signal as a function of time. Once the amplitude and phase of the sine time-function is known, motion signals at any time point can be calculated. The amplitude and phase parameters of the sine signal at each pixel can thus be estimated, and the motion signal at all pixels at a commonly aligned time grid can then be calculated. This method can be used to time-align pixels detected with different vectors within each zone or across zones.

Motion Signal Alignment: Synchronization Using $2\pi$ Shift of the Sine Motion Signal As yet another example, motion signals can be aligned based on the cyclic nature of tissue motions produced by continuous sinusoidal vibration of the transducer, in these instances, the motion signal at each spatial location is temporally repeated with a period of T. The period, T, is determined by the angular frequency, $\omega$, of the continuous vibration, $$T = \frac{2\pi}{\omega}; \quad (8)$$

therefore, the sine motion signal repeats itself over a phase difference of $2\pi$, or a time period of T. The motion signals from two imaging zones can thus be time-aligned by careful design of the time delay, $\Delta t$, in FIG. 6, such that, $$\Delta t = k \cdot T = k \cdot \frac{2\pi}{\omega} \text{ for } k = 1, 2, 3, \ldots. \quad (9)$$

Thus, by selecting the time delay according to Eqn. (9), the motion signals from different imaging zones are "automatically" aligned without the need of further time alignment.

Based on Eqns. (4) and (9), the vibration frequency, $\omega$; the detection $PRF_0$; the number of temporal samples, M; and the number of imaging vectors within each zone, N, can all be fine-tuned to fulfill the condition described in Eqn. (9).

Alternatively, a "wait time," $\varepsilon$, can be added between the detection zones such that, $$\Delta t = \frac{N \cdot M}{PRF_0} + \varepsilon. \quad (10)$$

As a result, the wait time, $\varepsilon$, can be conveniently adjusted to meet the requirement of Eqn. (9), or, the detection events for each zone can by initiated by an external trigger signal that is synchronized to a fixed phase over different cycles of the sine vibration signal. Note that within-zone alignment is still necessary to remove the time-delay induced by within-zone sequential tracking.

Motion Signal Alignment Within Zone Processing

Figure 7:
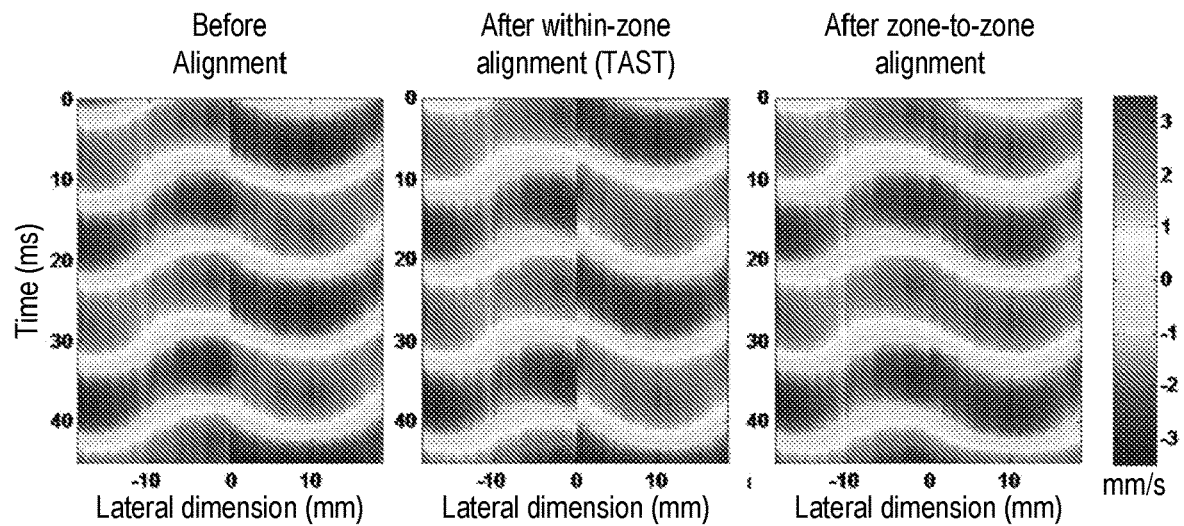
FIG. 7 illustrates an example of shear wave signal alignment using a phase-shift technique.

As can be seen in FIG. 7, after within-zone alignment, tissue motion signals within each imaging zone are aligned and ready to be used for calculation of mechanical properties. In some instances, however, instead of aligning motion signals across different imaging zones, tissue mechanical properties can be calculated within each individual zone, and then the estimates from different zones can be combined into a final map. In this way, discontinuities of the motion signal across zones would not matter. If there are small discontinuities in the final mechanical property map between zones, a spatial filter (e.g., a median filter) can be used to smooth the final mechanical property map. This approach is suitable for continuous transducer vibration shear waves because the primary shear wave propagation direction is top-to-bottom, away from the transducer. This propagation direction is primarily within zone with little across-zone, propagation, and thus makes calculation of tissue mechanical properties within each zone feasible.

Motion Signal Alignment Single Imaging Zone Detection

Another solution to the motion signal alignment problem is to avoid using multiple imaging zones (i.e., to use only a single imaging zone). Using a single imaging zone generally requires a large number of imaging vectors (i.e., a large value of N) to cover a sufficiently large imaging area. The challenge of this approach, however, is that the $PRF_e$ will be too low if N is very large. Low $PRF_e$ can be problematic in terms of causing aliasing, especially for transient and broadband shear waves produced by acoustic radiation force.

Figure 8:
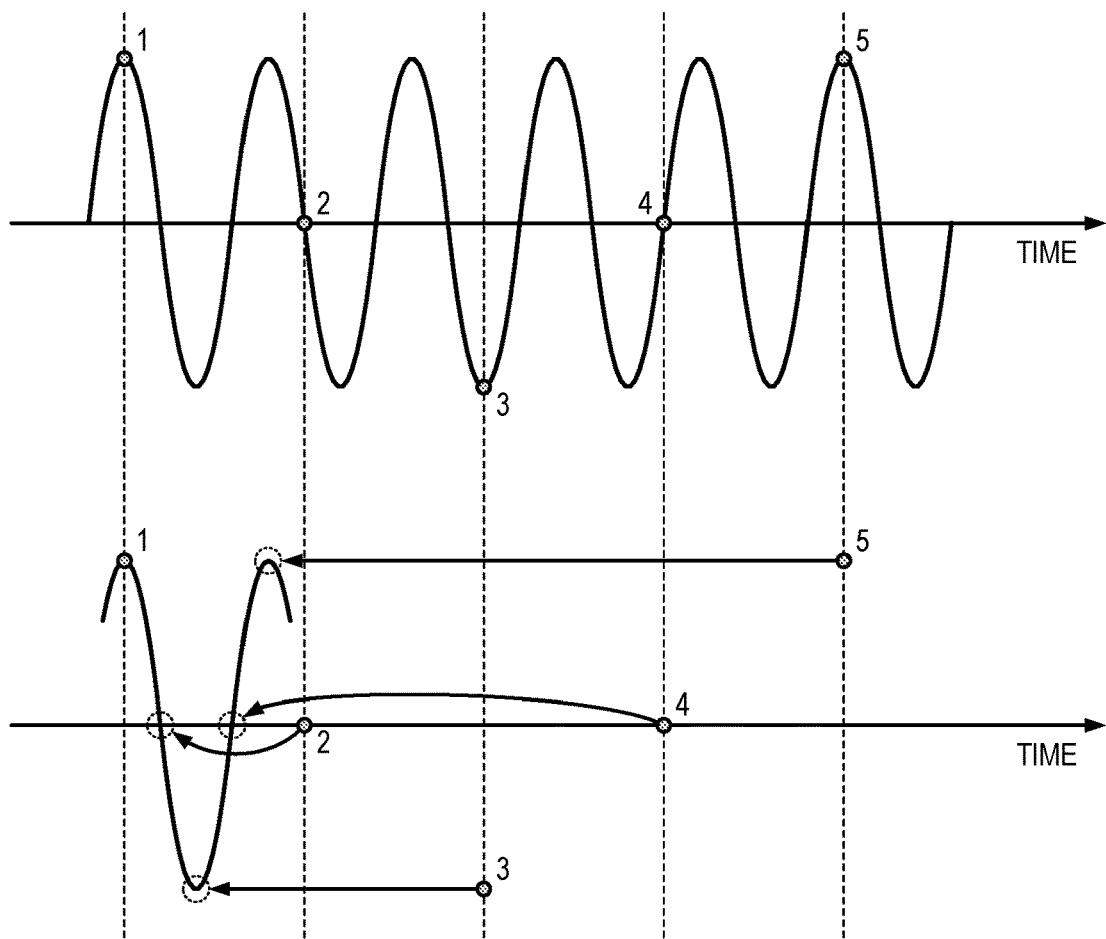
FIG. 8 illustrates a schematic plot of an aliasing correction method for low $PRF_e$ single imaging zone tissue motion detection. The upper panel shows the relationship between the actual sampling point and the sine wave signal. The lower panel shows the time-shifted sampling points that recover a non-aliasing sine signal.

However, for continuous tissue motion produced by transducer vibration, the aliasing can be corrected for by taking advantage of the cyclic nature of the sine wave used to drive the continuous vibration of the transducer. As illustrated in FIG. 8, the detection $PRF_e$ and the vibration frequency, $\omega$, can be carefully selected such that by shifting the pulse-echo events (represented as circles in FIG. 8) by integer multiple numbers of sine cycles, the non-aliased motion signal can be reconstructed.

In the example shown in FIG. 8, $PRF_e=0.8\omega/2\pi$, which causes aliasing. By shifting data samples 2, 3, 4, and 5 bp one cycle, two cycles, three cycles, and four cycles, respectively, the original sine signal can be reconstructed without aliasing. This can be done for each imaging vector within the single imaging zone to obtain non-aliased shear wave signals. After this step, additional time alignments across different vectors, as described above, can then be used to account for delays among vectors.

After correcting for effects of transducer motion (e.g., using the methods described above) and time delay in ultrasound pulse-echo motion detection, 2D shear wave signals at a common time grid can be used to calculate mechanical properties of tissue using standard elastography processing methods, such as Local Frequency Estimation ("LFE"), time-of-flight, direct inversion, and other methods.

It is assumed that the ultrasound transducer is vibrating at a single frequency in the examples given above. The methods described here can also be readily extended to situations where the continuous transducer vibration contains multiple sinusoidal frequencies, or a chirp signal. As such, mechanical properties can be measured over multiple frequencies.

The techniques above have been described for 2D elastography imaging using a 1D-linear ultrasound array transducer. These techniques are also applicable to single element, 1D curved array, 1.5D array, 1.75D array, and 2D array transducers. For single element transducers, the methods can be scaled down to 1D elastography. For 2D arrays, the methods can be extended to 3D elastography imaging. The correction of transducer motion and delay in ultrasound motion detection can also be combined together. The methods described here can also be used for measuring mechanical properties of tissues and non-tissue materials such as polymers.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for measuring a mechanical property of an object using an ultrasound system having a ultrasound transducer, the steps of the method comprising:
   (a) applying a continuous external vibration to the ultrasound transducer using at least one actuator attached to the ultrasound transducer to mechanically vibrate the ultrasound transducer, whereby applying the continuous external vibration to the ultrasound transducer induces at least one shear wave in the object in addition to causing a time-varying compressional deformation of the object;
   (b) acquiring shear wave motion data from the object using the ultrasound transducer while the continuous external vibration is being applied to the ultrasound transducer, wherein the shear wave motion data are indicative of the at least one shear wave propagating within the object, wherein the shear wave motion data comprise a plurality of frames, wherein each of the plurality of frames corresponds to the shear wave motion data acquired at one of a plurality of different time points;
   (c) estimating a plurality of compression profiles, wherein each one of the plurality of compression profiles is estimated by Fourier transforming the shear wave motion data to k-space, identifying spectral information associated with the plurality of compression profiles in the k-space, and Fourier transforming the identified spectral information to produce the estimating of the plurality of compression profiles, wherein each one of the plurality of compression profiles is estimated for a different one of the plurality of frames such that each of the plurality of compression profiles is indicative of the time-varying compressional deformation of the object caused by the continuous vibration of the ultrasound transducer at one of the plurality of different time points;
   (d) generating a combined compression profile by combining the plurality of compression profiles;
   (e) producing corrected data by separating the combined compression profile from the acquired shear wave motion data; and
   (f) processing the corrected data to calculate the mechanical property of the object.

2. The method as recited in claim 1, wherein the combined compression profile is removed from the shear wave motion data by subtracting the combined compression profile generated in step (d) from the shear wave motion data.

3. The method as recited in claim 1, wherein the ultrasound transducer is at least one selected from a group consisting of a single element transducer, a 1-dimensional array transducer, 1.5-dimensional array transducer, 1.75-dimensional array transducer, and 2-dimensional array transducer.

4. The method as recited in claim 1, wherein acquiring the shear wave motion data includes performing a data acquisition over at least one selected from a group consisting of one, two, or three spatial dimensions.

5. The method as recited in claim 2, wherein the combined compression profile is removed from the shear wave motion data by:
   generating a plurality of scaled compression profiles by scaling the combined compression profile for each of the plurality of frames, such that each of the plurality of scaled compression profiles corresponds to one of the plurality of frames; and
   subtracting each of the plurality of scaled compression profiles from the corresponding one of the plurality of frames.

* * * * *

UNITED STATES PATENT AND TRADEMARK OFFICE
CERTIFICATE OF CORRECTION

PATENT NO. : 12,023,199 B2
APPLICATION NO. : 15/766327
DATED : July 2, 2024
INVENTOR(S) : Daniel C. Mellema et al.

It is certified that error appears in the above-identified patent and that said Letters Patent is hereby corrected as shown below:

In the Specification

Column 1, Lines 53-54, "transducer the" should be --transducer (e.g., the--.

Column 5, Line 43, "awhile" should be --while--.

Column 6, Line 13, "approached, in" should be --approaches. In--.

Column 6, Line 59, "21)" should be --2D--.

Column 8, Line 15, "direction x-direction)" should be --direction (e.g., x-direction)--.

Column 9, Line 29, "FEN" should be --FEM--.

Column 12, Line 5, "Signed Alignment: Phase Shift Signed" should be --Signal Alignment: Phase Shift Signal--.

Column 12, Line 12, "motion, detected" should be --motion, $M_1$, detected--.

Column 13, Line 10, "transducer, in" should be --transducer. In--.

Column 14, Line 32, "bp" should be --by--.

Signed and Sealed this
Twenty-seventh Day of August, 2024

Katherine Kelly Vidal
*Director of the United States Patent and Trademark Office*